United States Patent [19]

Tucker

[11] Patent Number: 5,171,224
[45] Date of Patent: Dec. 15, 1992

[54] PROTECTIVE DEVICES FOR HANDLING BODY FLUID

[76] Inventor: Annabelle D. Tucker, 4480 Sherman Oaks Cir., Sherman Oaks, Calif. 91403

[21] Appl. No.: 695,535

[22] Filed: May 3, 1991

Related U.S. Application Data

[63] Continuation-in-part of Ser. No. 496,628, Mar. 21, 1990, which is a continuation-in-part of Ser. No. 556,204, Jul. 23, 1990, which is a continuation-in-part of Ser. No. 556,205, Jul. 23, 1990.

[51] Int. Cl.⁵ .............................................. A61M 5/50
[52] U.S. Cl. ..................................... 604/110; 604/192; 604/319
[58] Field of Search ...................... 604/110, 212–216, 604/403, 192, 198, 317–321; 206/364–366, 370, 813, 886

[56] References Cited

U.S. PATENT DOCUMENTS

| | | | |
|---|---|---|---|
| 2,663,463 | 12/1953 | Benbury et al. | 604/212 X |
| 3,308,998 | 3/1967 | Oppasser et al. | 604/212 X |
| 4,452,358 | 6/1984 | Simpson | 206/366 |
| 4,636,203 | 1/1987 | Emanis et al. | 604/257 |
| 4,836,373 | 6/1989 | Goldman | 206/366 |
| 4,890,734 | 1/1990 | Gach | 206/366 |
| 5,002,533 | 3/1991 | Jullien | 604/110 |
| 5,013,299 | 5/1991 | Clark | 604/114 |
| 5,020,665 | 6/1991 | Bruno | 206/366 |
| 5,024,666 | 6/1991 | Pituch | 604/263 |
| 5,047,019 | 9/1991 | Sincock | 604/192 |
| 5,078,695 | 1/1992 | Farrar, Jr. et al. | 604/192 |
| 5,078,696 | 1/1992 | Nedbaluk | 604/192 |
| 5,080,651 | 1/1992 | Jullien | 604/110 |

FOREIGN PATENT DOCUMENTS

| | | | |
|---|---|---|---|
| 0296406 | 12/1988 | European Pat. Off. | 604/110 |
| 2621825 | 4/1989 | France | 604/110 |

*Primary Examiner*—John D. Yasko
*Assistant Examiner*—Adam J. Cermak

[57] ABSTRACT

A protective system for handling body fluids that provides:
  (a) a device to receive and hold various sized needle caps in its resiliently, expandable, apertured, hollow top, that allows easy release of the held cap after one-handedly re-capping a used needle (sharp) for safe discard;
  (b) a device to needle suction a specimen of body fluid from a drainage system, directly into the resiliently, compressible transport container, through the needle topped, male adapter plug (or cap) of the container, to avoid open transfer of fluid to be tested;
  (c) a needle cap holding device that embodies a barbing surface to blunt the needle (sharp) tip prior to one-handedly re-capping the needle (sharp) for discard to avoid re-use that can chance exposure to hepatitis B, AIDS, etc.;
  (d) a device to hold needle caps that is a multi-use, multi-apertured, moveably adhereable, cost-effectively produced device to assure availability of a substitute second-hand, at the bedside, to hold a needle cap for safe recapping, where and when needed to avoid the chance of an accidental needle stick to clinician or unnoticed teammate, in the room;
  (e) a device to gently suction stimulate a capillary blood specimen from a skin puncture and contain it in the contact aperture of the removably attached firm cup-like collector.

5 Claims, 5 Drawing Sheets

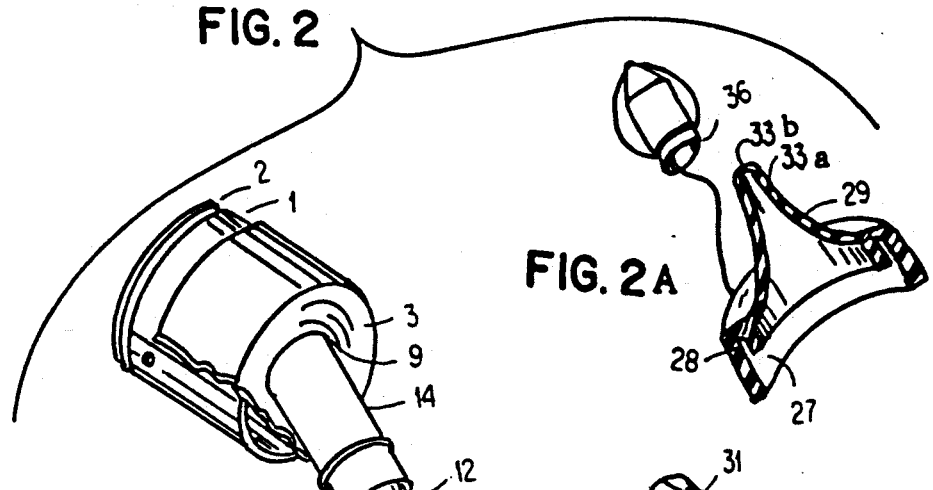
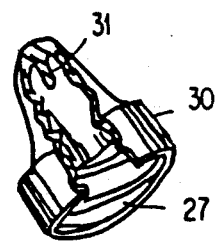
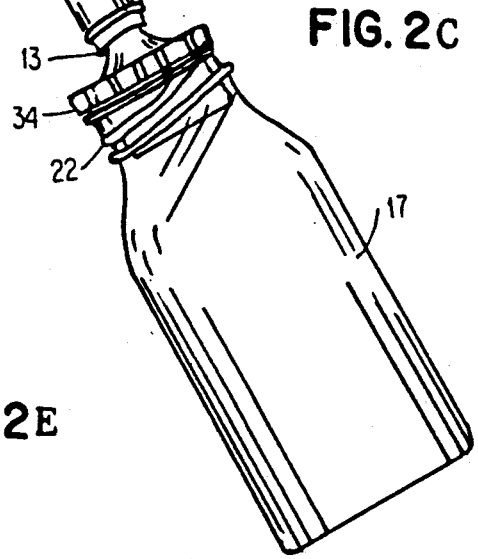
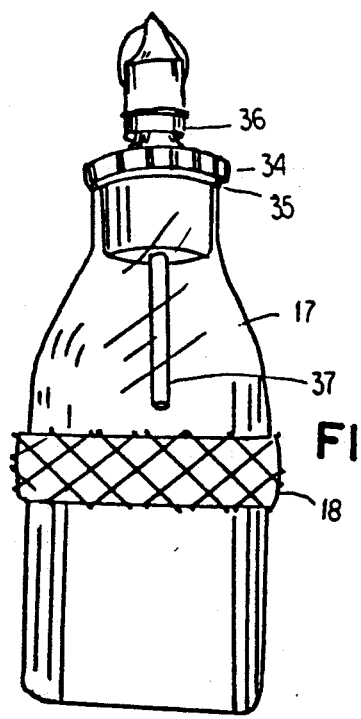
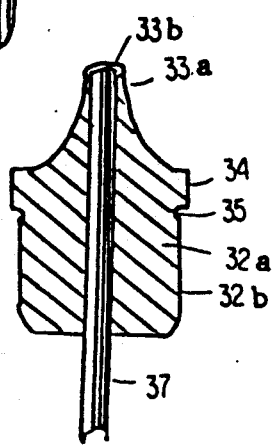
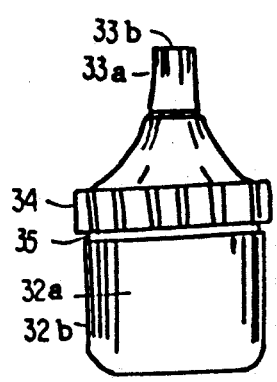

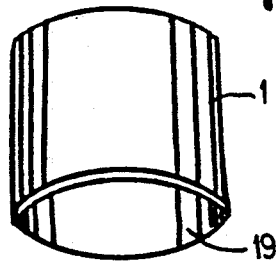
FIG. 11A
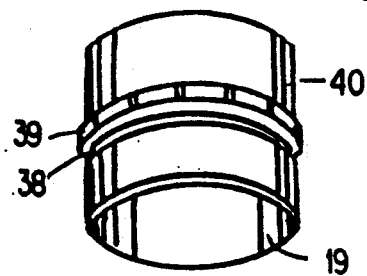
FIG. 12A
FIG. 11B
FIG. 12B
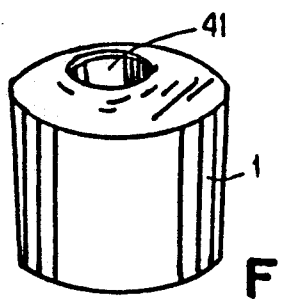
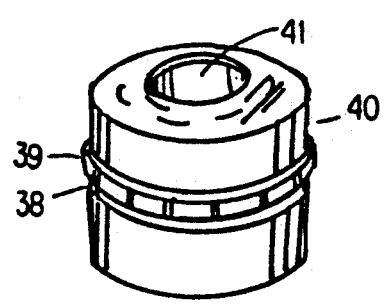
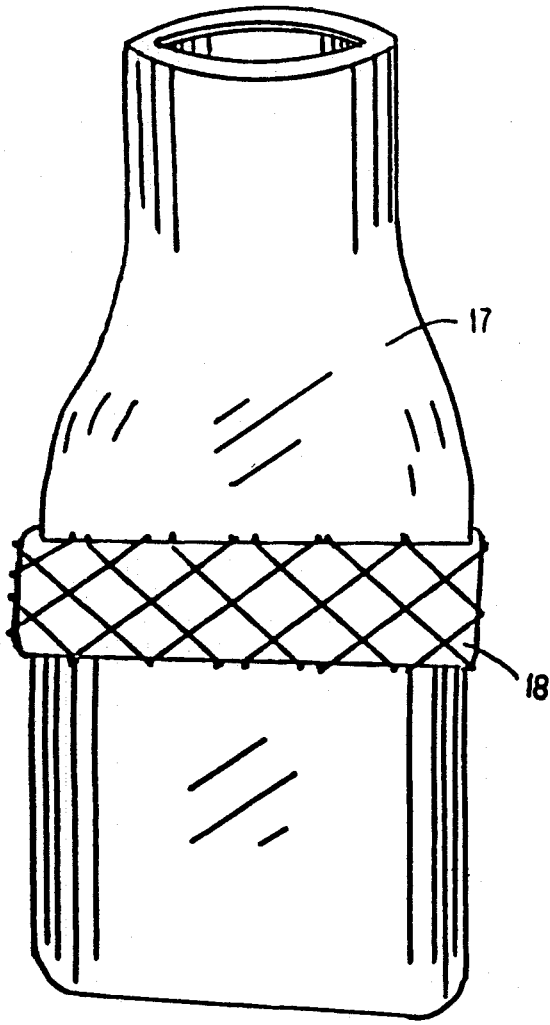
FIG. 11C
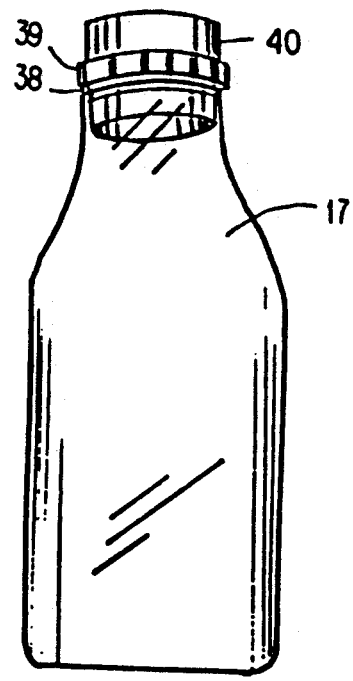
FIG. 12C

PROTECTIVE DEVICES FOR HANDLING BODY FLUID

RELATED APPLICATIONS

The related applications are: (CIP application) #07/496,628 filed Mar. 21, 1990 (CIP application) #07/556,204 filed Jul. 23, 1990 (CIP application) #07/556,205 filed Jul. 23, 1990.

Disclosure Documents are #243,557 filed Jan. 16, 1990 #243,896 filed Jan. 23, 1990 #256,943 filed Jul. 13, 1990 #273,382 filed Feb. 5, 1991.

BACKGROUND OF THE INVENTION

The present invention relates to a safety system for handling body fluids comprising devices to:
1. barb and safely recap used needles at the bedside;
2. suction needle draw a specimen from a fluid drainage system directly into the transport container;
3. to enclose a skin puncture wound with a suction collecting device to stimulate blood flow and capture capillary blood for testing a specimen One present invention relates to a bedside caddy device to assist clinicians in safely barbing and recapping a used needle (sharp) at the bedside, using only the one hand.

The protective cap for a skin invasive needle (sharp) is made to securely fit over that particular needle (sharp). The protective cap is intended to safeguard the needle (sharp) before and after use as an invasive device or contact with bloody body fluid.

An accidental needle stick to a clinician can mean hepatitis B, or worse, AIDS. The Center for Disease Control, protectively, tells us not to recap a needle (sharp). We must, at present, transport that unsheathed, contaminated sharp across the room, chancing an accidental needle stick to self or teammate Because of the pressured work schedules in hospitals or just out of habit, most clinicians continue to recap used sharps, as soon as they are withdrawn from the skin, by hand. Distraction from the patient can delay transporting the used sharp to discard container. Turning away from the area of use, can chance an accidental needle stick to an unnoticed teammate in the room. Recapping needles by hand knowingly chances a needle stick as our second hand, holding the cap, crosses over to approach the contaminated needle tip (A problem with some of the new devices). Safety, to a clinician is a capped, dirty needle—but it should be capped with one hand and at the bedside.

The problems with mishandling dirty sharps has increased the incidence of hepatitis B in clinicians and their contact, at an alarming rate. Many attempts are being made to solve the problem by industry. The concepts do increase the cost of the procedure and, thus, not available at the bedside when needed. Activation of the protective devices may be clumsy and unfamiliar to handle or cause our second hand to enter the contaminated field, and possibly initiate an accident. The direction of solutions seems to be aimed at the familiar device rather than a bedside second hand to protect our own.

The present invention is intended to provide that second hand needed at the bedside, moveably adhered adjacent to the area of an invasive procedure, ready to barb and safely recap a contaminated sharp used in the procedure. The present invention is also addressed to reducing the chance of body fluid contact with means to avoid open transfer of, possibly, bloody fluid, from one container to another, in needle specimen collection from drainage systems. A one-step procedure avoids the delay in recapping the dirty sharp immediately after bloody fluid contact.

Also addressed in the present invention is an alternate use of suction for specimen collection of capillary blood from a skin puncture At present, blood flow is stimulated to skin surface by milking the wound with fingers, chancing bruising of bone and tender tissue in the very young or elderly patient. Repeated procedures can possibly do permanent damage.

SUMMARY OF THE INVENTION

The theory of the invention is to avoid unnecessary contact with body fluids. Procedures should eliminate steps that openly handle the fluid. Contaminated (used) needles should be recapped with their mated cap, immediately after use, our second hand should never come toward the dirty needle tip nor should the used needle (sharp) leave the area of use until completely, securely and safely recapped.

One preferred embodiment of the present invention comprises a small firm cup with an overcap made of resiliant, expandable material that embodies one or more apertures in its top surface. The inside of the firm (polypropylene-like)support cup may hold a base fitted disc of hard material such as metal. Adhesive or a suction cup exterior base can moveably secure the assembled present device at the bedside. An aperture in the firm base, adjacent to its side wall, allows hooking the device onto the provided, intravenous pole hanger (the bedside caddy side clip), if desired.

Another preferred embodiment of the present invention comprises a squeezably resiliant container that receives, plug-like, a male adapter structure in its top opening for friction connecting to the hub of a needle for one step suction withdrawal and transport of a fluid specimen from a patient's drainage system.

A further object of this invention is to provide a novel device to secure a needle cap during a procedure and releasably hold it for one-handed recapping of a contaminated needle (sharp).

An additional object of this invention is to provide a firm area on which to barb (blunt) a used sharp and deter its reuse.

Another preferable object of this invention is to provide a needle support channel to the barbing (blunting) surface. The structure is secured within a top aperture of the invention by a groove that circumvents the outer upper surface of the barbing channel outer body. A support flange is formed to rest atop the aperture in the flexible overcap. The barbing channel supports the needle length during barbing pressure to prevent bending the needle. An additional object of this invention is to provide resiliant and expandable apertures in the top of the overcap to allow securing fit for the various sized needle caps and tubes. The expansible feature of the apertures allows easy release of the recapped needle to avoid the chance of an accidental uncapping when pulling out the capped syringe and needle structure for discard.

A further object of this invention is to provide a protective device to safeguard clinicians and their teammates against an accidental needle stick with a used sharp.

Another object of this invention is to deter the spread of hepatitis B and AIDS, through accidental needle sticks, to clinicians and their contacts.

An additional object of this invention is to provide a repositional, adhereable device that can be moved and secured at the area of need to immediately and safely recap a used needle.

A further object of this invention is to provide a cost-effective, reusable, and disposable device to afford its availability at every hospital bedside, to hold a needle cap ready for one-handed barbing and recapping a used needle (sharp) when an invasive, patient procedure is completed.

Another object of this invention is to provide a U-shaped clip to attach to an intravenous pole or bed rail. The clip would be used as a hanger for the needle cap holding device when the base aperture in the firm support cup is hooked onto the small free arm of the U-shaped clip.

A further object of this invention is to provide a device whose overcap is made of latex. The perforated mold is dipped and air blown to clear the apertures, in the top surface, of latex residue after dipping and before curing.

An additional object of this invention is to provide an alternate apertured, flexible overcap that is rubber molded, forming the apertures in the mold. The side clip may be formed as a part of the body of the overcap with the extended longer free, arm being coated with the rubber.

Another object of this invention is to provide an injection molded, alternative overcap made of a resiliant polyethylene-like material.

Another object of this invention is to provide a protective device whose firm support cup is made of a semi-rigid material, such as molded rubber, that can form a suction cup base as a part of the firm support cup body.

A further object of this invention is to provide a support label ring of non-resiliant material to hold the shorter U-shape arm of the side clip secure when the longer arm of the U-shaped clip is attached to an intravenous pole and the short arm is hooked under the lower rim of the flexible overcap.

An additional object of this invention is to provide a device that can be molded to form the apertured flexible overcap with a flared lower rim, open centrally and inner ridged to receive and hold the firm support base cup. The support cup would close the overcap base opening to complete the suction cup structure formed at the flared base of the overcap A further object of this invention is to provide a slightly larger aperture in the overcap top surface to accommodate the large diameter of a specimen tube or to allow easy access to the barbing surface when it is placed in the hollow bottom of the firm support cup to blunt the needle tip prior to recapping and discard.

Another object of this invention is to provide a movable device that can be positioned approximate the site of accessing a vein for insertion of a catheter The device would hold the cap for the stilette, ready for quick safe recapping when the stilette is removed from the catheter and blood return is observed.

Also an object of this invention is to provide an adhesive base that allows the device to be adhered to the side of a bed spring. The resiliant apertures allow retaining the needle cap at a horizontal angle needed to deter drips, when a fluid specimen is needle drawn from a drainage system. The fluid full syringe needle can be barbed on the rail and recapped with one hand and approximate the site of the procedure.

A further object of this invention is to provide a side clip that is U-shaped for use as an intravenous pole hanger that can double as a card holding clip. The clip can hold a diet alert, special care orders or identification for the patient in clear view at the bedside. The device can double as a flower tube holder with a gift card in the holding clip. The multi apertured device assures an available aperture for needle access when needed. The multi-use device assures its ready availability at time of need.

Another object of this invention is to provide a device that is simple to use, convenient, and enhances a routine familiar to clinicians avoiding the danger of unfamiliar equipment and changes of routine in the busy hospital setting.

Another object of this invention is to provide a squeezably resiliant container that gravity suctions, when squeezed and slowly released. An attached needle inserts to channel a fluid specimen from a patient's drainage system directly into what becomes the clean transport container when capped.

A further object of this invention is to provide the means for a one-step procedure for specimen collection of bloody body fluid to prevent the possible splash in open transfer of fluid to a second container for transport to lab and delays in needle recapping.

Another object of this invention is to provide a grippable male adapter top opening for the specimen container that receives the needle hub for withdrawing a specimen. The male adapter is then easily removed to access the specimen for dip stick testing.

Also an object of this invention is to provide a cap for the male adapter that plugs the aperture for safe transport of the fluid specimen.

Another object of this invention is to provide an extended tubular channel that opens through the male adapter aperture inlet passing through, and as a part of, the lower body of the adapter that forms a plug for the container. The extended tube of the channel prevents accidental spills if the container is tilted during a specimen draw or needle recapping and removal procedure prior to sealing the container for transport.

Also an object of this invention is to provide an alternate screw-on inner flanged male adapter that mates with the threads on the neck of the specimen container and sealably seats on its top rim. The male adapter aperture is sealed with a friction cap after needle is barbed, capped and discarded.

A further object of this invention is to provide a needle cap holder that can be adhered in a horizontal position and still retain the needle cap. The needle on the fluid filled container can then be recapped safely and without danger of a fluid spill.

Another object of this invention is to provide a suction means to cover the wound and stimulate capillary blood flow from a skin puncture for collecting a specimen for laboratory testing.

A further object of this invention is to provide a firm, apertured hollow cup that fits into the opening of the suction means. The aperture in the flat surface of the cup base forms the top suction access to stimulate blood flow and capture the pooled blood from the skin puncture site.

Another object of this invention is to provide an easily removable, apertured, hollow, firm cup to fit partially into the top opening of the squeezably resiliant suction means to allow easy access to the captured blood if pooled blood is scooped onto the flat inner surface surrounding the suction aperture in the firm cup.

A further object of this invention is to provide an alternate means of stimulating blood flow from a skin puncture. Use of fingers to milk a wound is damaging to tender tissue. A suction means can manipulate the wound area in a gentler manner as it stimulates the flow of blood.

Further features and advantages of this invention will become more apparent from the following description, the appended claims thereto, and the drawings.

BRIEF DESCRIPTION OF THE DRAWINGS

The accompanying drawings illustrate the invention. In such drawings:

FIG. 2 shows a partial cross sectional perspective view of the needle capper of the present invention in horizontal position, holding the needle cap for recapping the barbed needle on the fluid filled specimen container.

FIG. 2B shows a cross sectional perspective view of the mated screw-on male, container top, adapter for a needle and the attached friction cap that will seal the aperture of the adapter.

FIG. 2C shows a partial cross sectional perspective view of the alternate screw-on cap with its inner top plug to fit the aperture in the top of the male adapter plug to seal fluid within the specimen collector for transport.

FIG. 2D shows a flat view of the hollow male adapter plug.

FIG. 2E shows a flat view of the fluid filled specimen container with the top aperture of the alternate extended channel of the male adapter plug friction capped and ready for transport to the laboratory.

FIG. 2F shows the solid male adapter plug with the tube-like channel of the inlet extended beyond the base of the plug.

FIG. 11A shows a perspective view of the hollow interior of the alternate plug for the suction container.

FIG. 11B shows a perspective view of the apertured top surface.

FIG. 11C shows the suction squeeze container in a perspective view.

FIG. 12A shows the apertured cup plug for the suction squeeze container inlet with an annular grip and seating groove on the exterior surface.

FIG. 12B shows a perspective view of the apertured top of the plug.

FIG. 12C shows a suction container with the inlet plug in place.

DETAILED DESCRIPTION OF THE PREFERRED EMBODIMENTS

Figure 1:
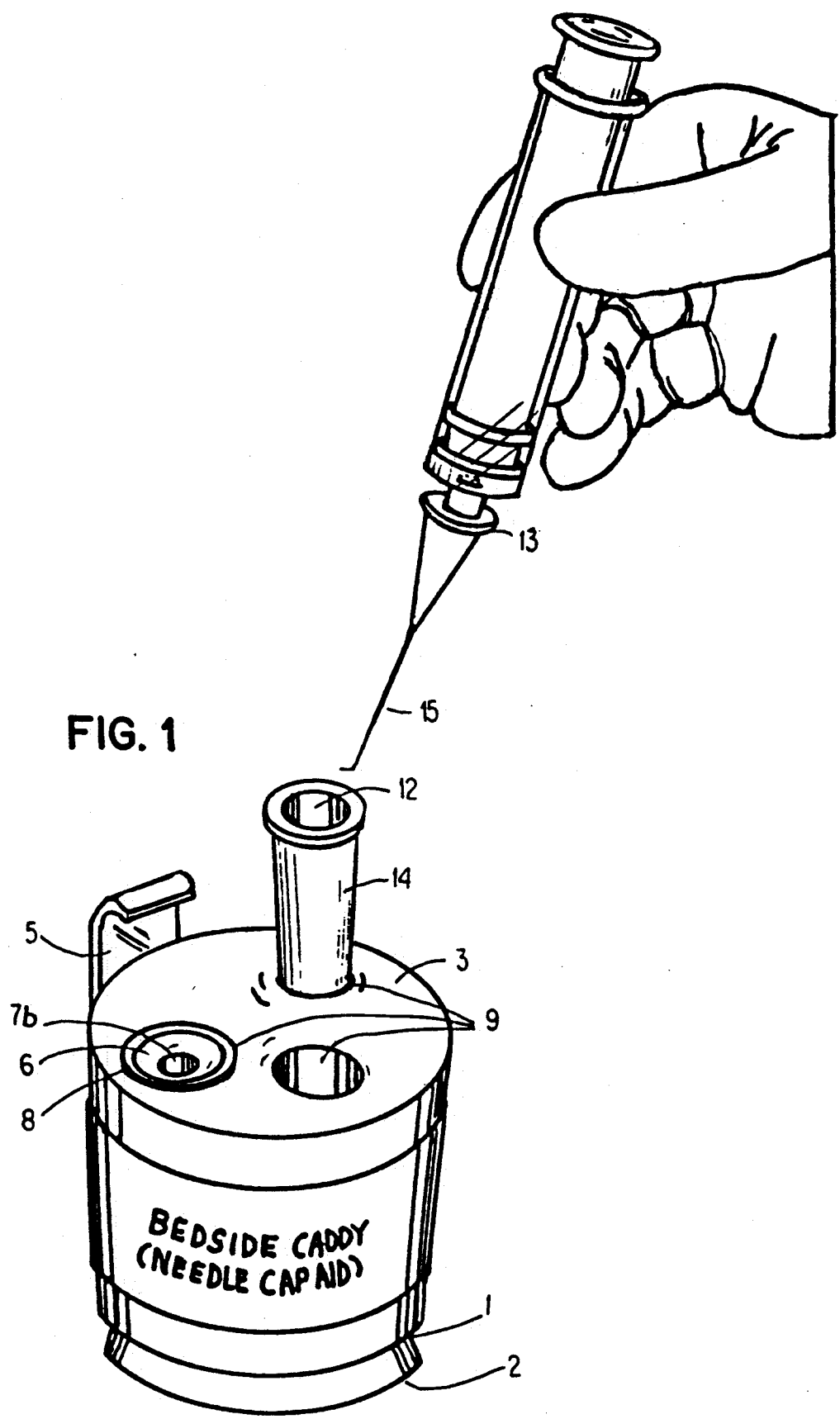
FIG. 1 shows a perspective view of the assembled present invention in use as a needle (sharp) barber and capping aid.
Figure 3:
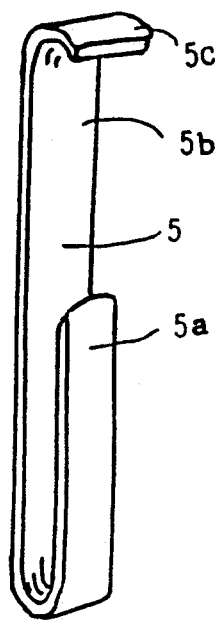
FIG. 3 shows a perspective view of the U shaped side clip.

Referring now to FIG. 1 there is shown a used and barbed needle 15 on a syringe, being held with one hand, aiming at the interior of a securely held needle cap 12. The needle cap 12, mated to the barbed needle 15, is in a position for safe recapping the used, barbed sharp 15 prior to leaving the site of use, and before its disposal. The needle cap 12 is secured within a resiliant, expandable aperture 9 atop the flexible overcap 3 of the present invention. The flexible overcap 3 expands to securely cover the firm open, hollow 19 support cup 1, within its hollow interior 20. The assembled structure of the present invention forms a hollow vault 20, 19 as shown in FIGS. 5A, 5B, 8A, 8B and 9, unassembled. The interior of the vault is accessed through the top apertures 9 in the flexible overcap 3 and the base aperture 16, shown in FIG. 5A and 5B, of the support cup 1 The needle barbing surface, in this instance, is at the base of a funneled support channel 7 to guide the needle to the barbing surface without bending the needle during pressure to blunt the needle tip The needle barber post 6, shown in FIG. 6, is circumvented with an outer groove 8 near the top rim of its outer body 6 surface. The groove 8 forms a top flange to rest atop the lip of the resiliant aperture 9 when gripped within the groove 8 on the barbing post 6 giving it stability in use. The U-shaped side clip 5, shown in FIG. 3 provides a shorter arm 5a to hook under the lower rim of the flexible overcap 3. In this instance, the longer arm 5b is left adjacent the outer side wall of the overcap 3, openly free to act as a secured clip 5 on the body of the overcap. The shorter arm 5a is secured in place by pressure from the annular label ring 4 that slides over the body of the flexible overcap 3. The annular label ring 4 may be formed from a strip whose free ends are sealed in a known manner to allow a tight hold on the imbedded side clip's shorter arm 5a. The U shaped side clip 5 may have a top barrier 5c that is a top bend or side wings formed of the rubber coating during the rubber molding. The barrier 5c, 5d, can prevent slipping when pressure is applied in recapping if the clip 5 is taped to an intravenous pole or side rail and held by the longer arm 5b of the U shaped clip 5.

In FIGS. 2A and 2B there is shown the present invention with one aperture 9 in the flexibly resiliant overcap 3. The adherent base 2 of the support cup 1 is attached in a horizontal position to a bed spring to receive and securely hold the protective cap 14 for the needle 15 on a fluid specimen withdrawal container 17. When a specimen is needed from a drainage system, the needle cap 14 placed in the resiliant aperture 9 of the present invention ready to safely recap the needle 15 on the fluid filled container 17. The horizontal position of the secured needle cap 14 helps prevent fluid spill through the needle 15 during recapping. Using the suction withdrawal container 17, with a male adapter plug 33 to retain the needle 15 for fluid specimen collection allows a one step procedure to reduce handling of the needle 15 and body fluid that chances contamination. This horizontal recapping procedure enhances the one step specimen collection by capping the needle 15 in a safe manner prior to removing the capped (14) needle 15 to allow sealing the male adapter plug 33 opening for clean transport of the specimen to the laboratory.

The male adapter plug may have a solid base with a central tubular channel 37 from the male adapter inlet 33 extending through and past the base of the plug 32. When assembled in the top opening of the suction container 17 as seen in FIG. 2E, the tube 37 extends within the interior of the container 17 to prevent spill of collected fluid if the container 17 is tilted. An alternate adapter seen in FIG. 2D has a hollow base 32. Alternate means of capping the male adapter plug 33 are friction plugs 36 or screw 27 on plug (31) caps 30. Alternate male adapters may be a screw-on 27 cap 29 with an inner flange 28 to avoid leaking when placed over and into threaded the top opening 22 of the squeezably resiliant fluid collection and transport container 17. Barbing the needle 15 prior to recapping and removal for discard may be done against the metal bed spring frame.

FIG. 3 shows the side clip 5 with a top bend to provide a barrier 5c at the top of the hardened spring metal clip 5. The shorter arm 5a of the clip 5 is formed by a bend in the body of the clip 5 to return a part upon itself in a parallel, slightly separate position forming a U-shape with the longer remaining body part 5b.

Figure 4:
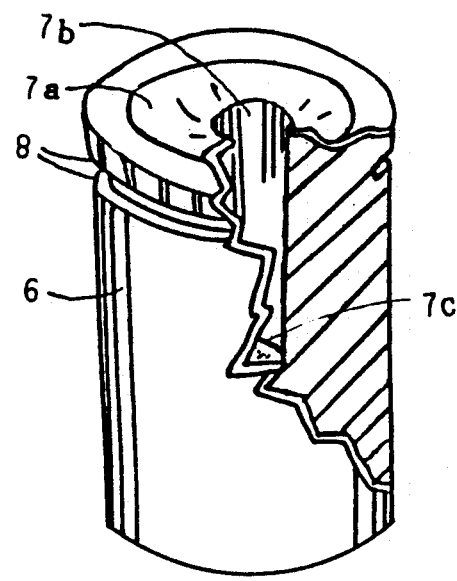
FIG. 4 shows a perspective view, partially cut-away, of the needle barber and its needle support channel.

FIG. 4 shows the needle barbing post 6 in partial cut-away to expose the inner structure of the needle support channel 7B with the funnel entrance 7A to direct the needle 15 and to 7B and to barbing surface 7C at the base of the channel 7B. The annular groove 8 is shown circumventing the near top outer surface of the barbing post 6. The annular groove 8 is used to stabilize the barbing post 6 within the aperture 9 of the flexible overcap 3. The base of the barbing post 6, when in position within the aperture 9, rests on the inner base of the support cup 1 to sustain the pressure of the barbing procedure.

Figure 5A:
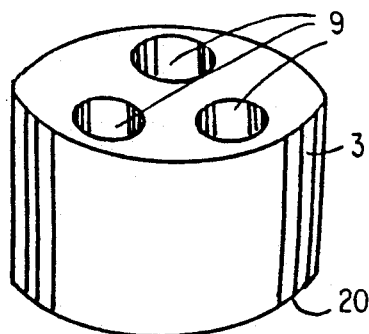
FIG. 5A shows the top apertures of the needle cap holding device.
Figure 5B:
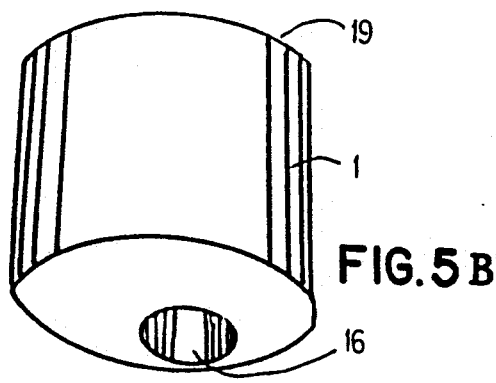
FIG. 5B is a perspective view of the apertured base of the device.
Figure 6:
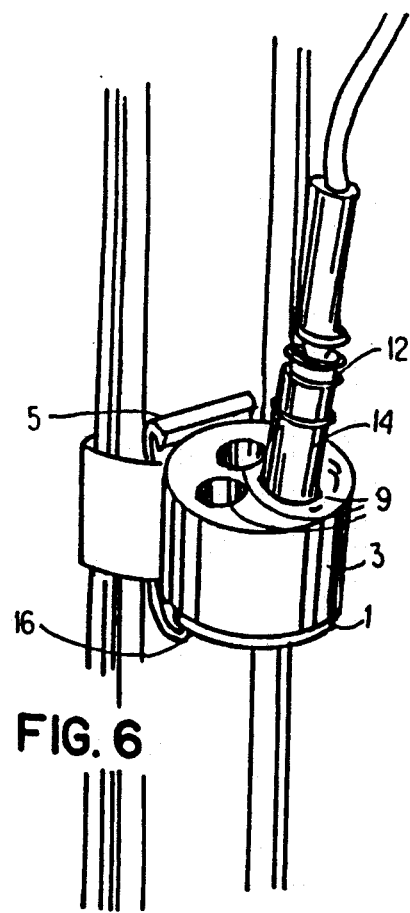
FIG. 6 shows a perspective view of the present invention assembled and in use on an intravenous pole.

FIG. 5A shows the resiliant, flexible overcap 3 with multi-apertures 9 in position to cover the hollow opening 19 and outer sides of the firm support cup 1. The support cup 1 base shows an aperture 16 adjacent the outer base rim to receive the shorter arm 5a of the side clip 5. Using the base cup aperture 16 to hook onto the side clip arm 5a strengthens the assembly for use on an intravenous pole as shown in FIG. 6. The longer arm 5b of the U-shaped clip 5 is taped to the pole and the assembled needle cap holder is hooked onto the exposed shorter arm 5a of the clip 5 through the base cup 1 aperture 16.

Figure 7:
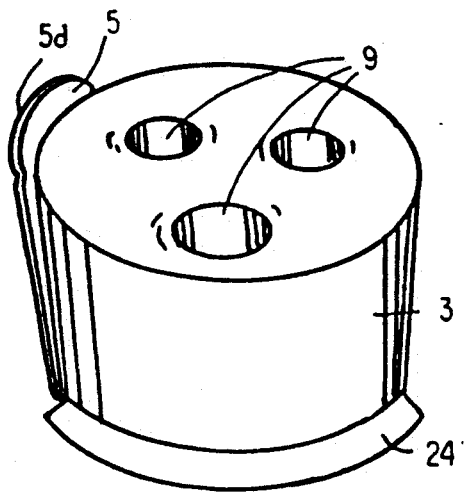
FIG. 7 shows a perspective view of the assembled present invention with the alternate suction cup semi-rigid base support.

FIG. 7 is an assembled needle cap holder using a molded suction cup 24 with a support cup hollow top 19 covered with the resiliant, expandible apertured overcap 3. The side clip is coated with material that provides a barrier top in wing like side extension 5d of the coating material such as rubber.

Figure 8A:
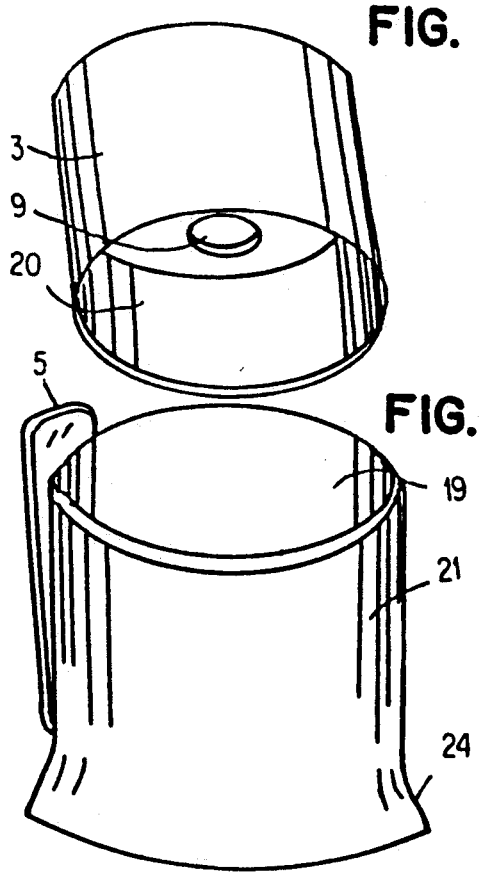
FIG. 8A is a perspective view of the apertured top inner surface of the alternate form of the holding device for a cap for a sharp.
Figure 8B:
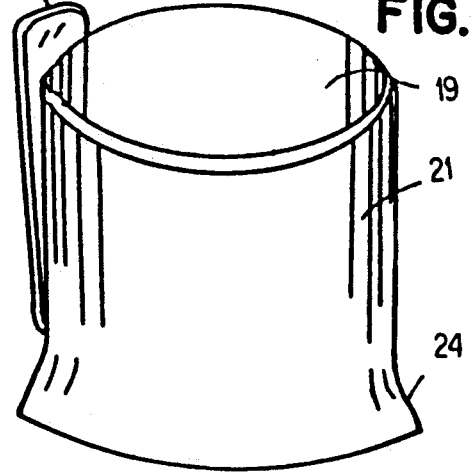
FIG. 8B is a perspective view of the alternate base for the device showing the suction cap base and side clip as a part of the base structure.

FIG. 8A and 8B show the hollow interior of the top apertured overcap 3 ready to be stretched over the semi-rigid support 21 of the suction cup base 24 structure. The suction cup base 24 for the needle cap holder is to provide a more permanent means of attachment at the bedside rather than depend on a repositional adhesive when extended use is anticipated.

Figure 9:
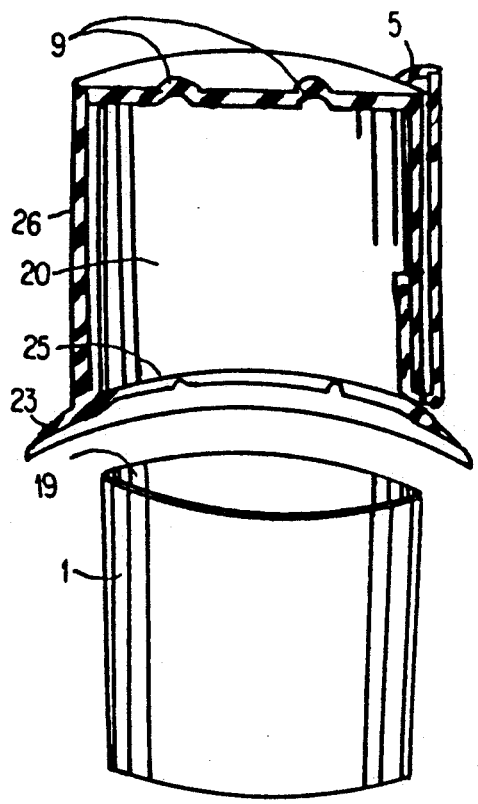
FIG. 9 shows a perspective view of the partially cut-away structure of the apertured flexible overcap with a flared lower rim and an inner ridge to hold the shown support cup in the hollow interior to form a closed suction cup base when assembled.

In FIG. 9 there is shown an alternate suction base for the needle cap holder that is an extention of the resiliant, flexible lower rim of the overcap 3. The flanged base rim 23 of the overcap 3 has an open inner ridged base to receive the firm support cup 1. Insertion of the firm cup 1 to rest its base above the sealing inner ridge 25 allows the extended flange 23 to act as a suction cup 23 to secure the needle cap holder at the bedside. The more permanent means of attachment increases the chance for using the needle cap holder as the bedside caddy to hold tubed flowers, cased thermometers, pens, pencils, etc. The side clip 5 can hold special orders, diet alert additional identification or greeting cards and messages.

Figure 10A:
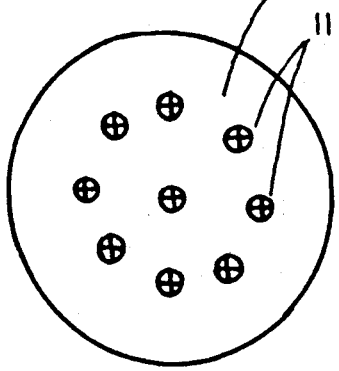
FIG. 10A shows a top elevational view of the dimpled (non-slip) metal or firm barbing disc that lies flat within the support cup of the present invention.
Figure 10B:
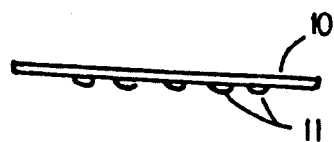
FIG. 10B shows a side view of the needle tip barbing base plate shown in FIG. 10A.

FIGS. 10A and 10B show a metal or hard disc 10 as an alternate barbing surface to blunt used needles. The disc 10 is dimpled 11 to avoid a needle 15 slipping with blunting pressure. The disc 10 fits within the support cup base 1-21 to lie flat on the bottom surface to be accessed through an aperture 9 in the flexible overcap 3. The side view of the disc shows the dimpling 11 on the disc 10 surface. Barbing the used needle 15 tip deters potential re-use that could chance an increase in the spread of hepatitis B and AIDS.

In FIG. 11A and 11C the hollow 19, apertured, firm support cup 1 may be alternately used to fit into the top opening of the squeezably resiliant container 17. The apertured (16) cup base 1, exposed as the top outer surface, becomes a suction access from interior of the container 17 when finger pressure on the collapsed container 17 is released. An annular gripping ring 18 is shown on the body of the container 17 to assist grip and strengthen the container wall to increase strength of suction force when aperture 4 of cup 1 spans a skin puncture to draw blood. In FIG. 12A-12C an annular groove 38 has been added to encircle the body of the aperture 41 firm support cup 1 to catch on the inner lip of the squeezably resiliant container 17 opening to limit and secure insertion of the cup 1 into the opening. An annular gripping ring 39 has been added to encircle the body of the support cup 1 to seat onto the container 17 opening allowing easier insertion and removal of the plugged-in cup 1. In FIG. 9 there is shown an alternate suction base 23 for the needle cap holder that is an extention of the resiliant, flexible lower rim of the overcap 3. The flanged, base rim 23 of the overcap 3 has an open inner ridged 25 base to receive the firm support cup 1.

In the foregoing descriptions, specific examples have been used to describe the invention. It is understood by those skilled in the art that certain modifications can be made to these examples without departing from the spirit and scope of the invention.

I claim:

1. A protective apparatus for the closed collection of bloody body fluid specimens, for laboratory testing, using a sharp to access said fluid, when necessary, that comprises:

a holding container for the cap of a sharp being used in the body fluid collection procedure, said container having side walls, an adhereable outer base, at least one expandible apertures in a top surface which at least one aperture channels to communicate with an inner firm surface of a needle tip barbing base plate and hold the cap, for said sharp, securely ready for one-handed re-capping of the blunted sharp into its cap held in the expandible apertured channel, immediately on removal from bloody body fluid access, of the repositionably adhereable holding container;

a non-dispensing suction container with flexibly resiliant side walls, a flat base and an inlet for seating a plug that allows air exchange, responsive to squeezing on the side walls of said suction container, through an opening from said plug apex to an interior chamber formed by said suction container in a manner that by-passes, and thus deters loss or leaking of, the accessed bloody body fluid being collected by the suction means, within the assemblage, that becomes the means to cleanly transport the specimen to the laboratory in a one-step procedure after said plug apex is capped, avoiding the need to openly transfer bloody fluid into a secondary specimen container.

2. The protective apparatus for the closed collection of bloody body fluid specimens as described in claim 1 wherein the plug for the non-dispensing suction container inlet has a top projection forming a male adapter for the hub of a needle or straw or for insert into a non-needle valve access to pooled fluid, said top projection of said plug delimited by an apex and a bore extending through said plug member and a tubular base extension of the bore from said apex and opening into said chamber in a central position to contain the bloody body fluid within said chamber and deter accidental dispensing of said fluid when said container is re-squeezed or tilted during the specimen collection suction procedure or during transport-to-laboratory in said suction container which is to be capped at the apex bore atop the male adapter projection for safe transport.

3. The protective apparatus for the closed collection of bloody body fluid specimens as described in claim 1 wherein the plug of the non-dispensing suction container inlet has a hollow, top apertured projection with an open base to allow for air exchange, between said top aperture and is a suction container interior chamber, said top aperture having a surrounding flat surface and an inner surface which forms a shelf to collect and hold the bloody fluid away from the air exchange path during suction container procedure to force accessed blood from a stab wound through the skin contact aperture of said plug top flat surface on to the inner shelf of said plug in a closed manner, providing a one-step means of transporting a bloody body fluid specimen to the laboratory when the hollow plug container is sealed for transport, said stab wound having been made with a sharp whose cap is held within a top aperture channel of said holding container for the cap of a sharp to quickly secure the dirty sharp into its held cap, using only one hand, prior to leaving the site of use to transport said sharp to the discard area.

4. The protective apparatus for the closed collection of bloody body fluid specimens as described in claim 1 wherein said adhereable outer base of said holding container for the cap of a sharp is a suction cup base to secure it to the area adjacent the use of a sharp.

5. The protective apparatus for the closed collection of bloody body fluid specimens as described in claim 1 wherein the holding container for the cap of a sharp has a side clip that is anchored within the base structure of said holding container to bend up along the exterior side of said container sidewalls for purposes of securing an identification card or order sheet for the patient, said side clip being a securing means of attachment to an intravenous pole when tape is used around the clip and said pole when no flat surface is adjacent of the site of use of the sharp, used to access bloody body fluid, and the cap, for the used sharp, is held within the apertured top open channel of the said holding device to allow one-handed safe re-capping of the used sharp immediately on removal from bloody body fluid access and without moving away from the site of sharp use to perform the protective procedure of barbing and one-handedly recapping a used sharp.

* * * * *